US009675783B2

(12) United States Patent
Asaad et al.

(10) Patent No.: US 9,675,783 B2
(45) Date of Patent: Jun. 13, 2017

(54) INTRACRANIAL FIXATION DEVICE

(71) Applicant: Brown University, Providence, RI (US)

(72) Inventors: Wael F. Asaad, Westwood, MA (US); David J. Segar, Providence, RI (US)

(73) Assignees: BROWN UNIVERSITY, Providence, RI (US); RHODE ISLAND HOSPITAL, Providence, RI (US)

( * ) Notice: Subject to any disclaimer, the term of this patent is extended or adjusted under 35 U.S.C. 154(b) by 55 days.

(21) Appl. No.: 14/528,580

(22) Filed: Oct. 30, 2014

(65) Prior Publication Data

US 2015/0141926 A1 May 21, 2015

Related U.S. Application Data

(60) Provisional application No. 61/905,264, filed on Nov. 17, 2013, provisional application No. 62/006,806, filed on Jun. 2, 2014.

(51) Int. Cl.
| | |
|---|---|
| *A61M 25/04* | (2006.01) |
| *A61B 5/00* | (2006.01) |
| *A61N 1/05* | (2006.01) |
| *A61M 25/02* | (2006.01) |
| *A61M 39/02* | (2006.01) |

(52) U.S. Cl.
CPC .......... *A61M 25/04* (2013.01); *A61B 5/6882* (2013.01); *A61M 25/02* (2013.01); *A61M 39/02* (2013.01); *A61N 1/0539* (2013.01); *A61B 5/6864* (2013.01); *A61M 2210/0687* (2013.01)

(58) Field of Classification Search
CPC ... A61B 5/6864; A61B 5/6882; A61B 5/6883; A61M 2210/0687; A61M 25/02; A61M 2025/0286; A61M 2025/0293; A61M 25/04; A61M 39/02; A61N 1/0539
See application file for complete search history.

(56) References Cited

U.S. PATENT DOCUMENTS

| | | | | |
|---|---|---|---|---|
| 4,328,813 | A | | 5/1982 | Ray |
| 4,874,380 | A | * | 10/1989 | Hesketh ............... A61M 25/02 128/DIG. 26 |
| 5,224,935 | A | * | 7/1993 | Hollands ............... A61M 25/02 128/DIG. 26 |
| 5,464,446 | A | | 11/1995 | Dreessen et al. |
| 5,865,842 | A | | 2/1999 | Knuth et al. |
| 5,927,277 | A | * | 7/1999 | Baudino ............. A61N 1/0539 600/386 |

(Continued)

*Primary Examiner* — Quynh-Nhu H Vu
(74) *Attorney, Agent, or Firm* — Douglas Denninger

(57) ABSTRACT

A fixation device including a base structure such as a faceplate having an inferior surface capable of contacting a surface of a skull of a patient, having a superior surface, and defining at least two securement features. Each securement feature can be engaged by a cranial fastener to attach the faceplate to the skull. The device further includes a fixation structure such as an alignment plate or a flexible fixation member carried by the base structure and positionable at least one of (i) over an opening in the skull and (ii) within an opening in the skull. At least one surface of the fixation structure defines at least one channel in which an intracranial device is capable of being placed, and further defines at least one fixation feature to enable the intracranial device to be secured to the fixation device.

6 Claims, 12 Drawing Sheets

(56) References Cited

U.S. PATENT DOCUMENTS

| | | | |
|---|---|---|---|
| 5,954,687 A * | 9/1999 | Baudino | A61M 25/02 604/174 |
| 6,044,304 A | 3/2000 | Baudino | |
| 6,134,477 A * | 10/2000 | Knuteson | A61M 25/02 607/115 |
| 7,988,674 B2 * | 8/2011 | Adams | A61B 5/6864 604/174 |
| 8,021,341 B2 * | 9/2011 | Lampropoulos | A61M 25/02 604/180 |
| 2006/0095009 A1 * | 5/2006 | Lampropoulos | A61M 25/02 604/174 |
| 2011/0190857 A1 | 8/2011 | Gerber et al. | |
| 2012/0130424 A1 | 5/2012 | Sengun et al. | |
| 2012/0232627 A1 | 9/2012 | Swoyer et al. | |
| 2013/0261664 A1 | 10/2013 | Spenciner et al. | |
| 2014/0155860 A1 * | 6/2014 | Behymer | A61N 1/0539 604/500 |
| 2014/0276418 A1 * | 9/2014 | Nelson | A61M 5/158 604/151 |
| 2014/0276529 A1 * | 9/2014 | Bodner | A61M 25/02 604/500 |

* cited by examiner

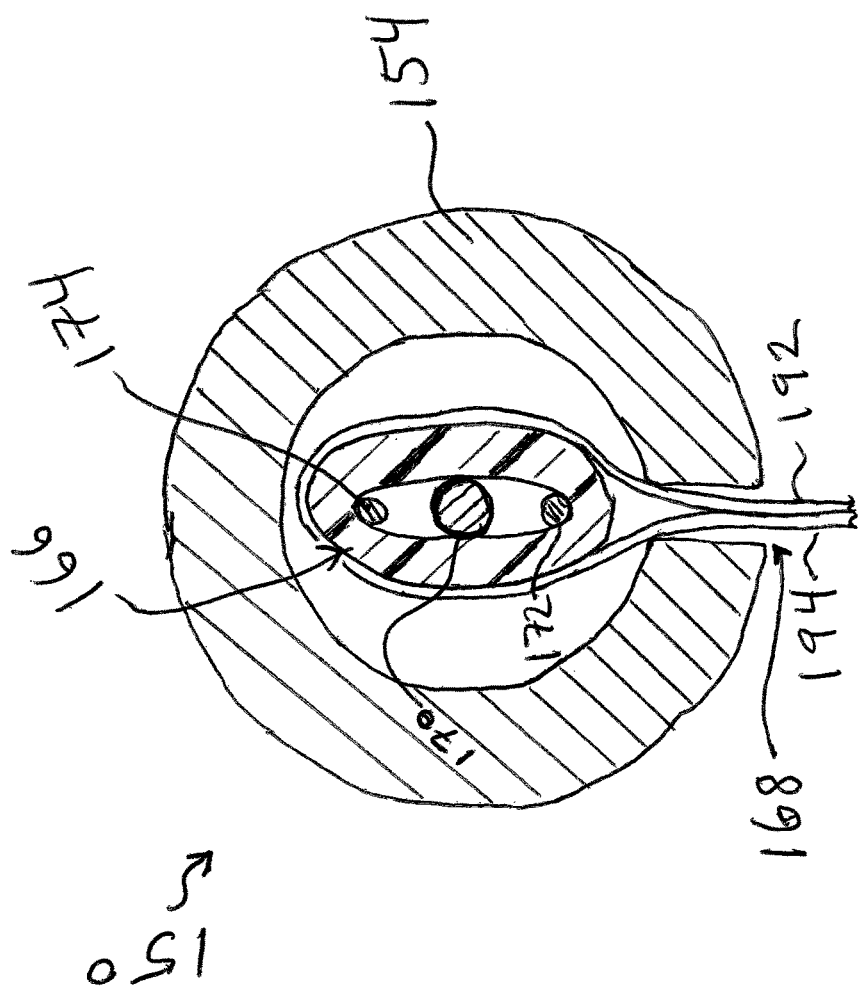
FIG. 9A (August 2016)

INTRACRANIAL FIXATION DEVICE

CROSS-REFERENCE TO RELATED APPLICATION

This application claims priority to U.S. Provisional Application Nos. 61/905,264 and 62/006,806 filed 17 Nov. 2013 and 2 Jun. 2014, respectively. The entire contents of each of the above-mentioned applications are incorporated herein by reference.

FIELD OF THE INVENTION

The invention relates to fixation devices that secure medical devices in a fixed position and more particularly to securing intracranial devices extending through an opening formed in a cranium of a patient.

BACKGROUND OF THE INVENTION

There are a number of conditions for patients where it is desirable to accurately position a probe, catheter, or other device within a brain of a patient by passing the device through a burr hole or other opening in the cranium of the patient. Intracranial probes include deep brain stimulating electrodes, recording electrodes, optical probes, and dialysis probes. Intracranial catheters include fiber optic catheters, injection cannulae, aspiration cannulae and fluid shunts. These intracranial devices are generally inserted through a burr hole during neurosurgery utilizing a guide system involving MRI (Magnetic Resonance Imaging), CT (Computed Tomography), or a stereotactic instrument, and are intended for positional placement in relation to selected anatomy of the patient. Many such intracranial devices are secured in place during or after surgery for use over an extended period of time and require accurate and reliable fixation in relation to the initial placement and patient anatomy.

Reliable fixation is essential to successful treatment utilizing intracranial devices such as electrodes or electrical probes which may have a dramatically different therapeutic effect if their position within a brain is shifted by only a few millimeters. Shunts and other catheters can become rapidly blocked or gradually occluded if intake ports are moved into an unintended position against existing tissue or are moved too close to dynamic cell layers such as found in choroid plexus.

A number of currently available fixation devices are complex, time-consuming to implement, overly high-profile with poor cosmetic results, and/or prone to failure. Several brain lead anchoring systems are disclosed by Ray in U.S. Pat. No. 4,328,813 and by Dreessen et al. in U.S. Pat. No. 5,464,446. Other anchoring systems are described by Knuth et al. in U.S. Pat. No. 5,865,842 and by Baudino in U.S. Pat. No. 6,044,304. Alternative anchor systems are discussed by Gerber et al. in U.S. Patent Pub. No. 2011/0190857 and by Swoyer et al. in U.S. Patent Pub. No. 2012/0232627, for example.

It is therefore desirable to have a simple, secure, reliable device to hold intracranial devices fixedly in a selected position.

SUMMARY OF THE INVENTION

An object of the present invention is to provide an improved intracranial fixation device which is easy to use yet is accurate and reliable over time.

Another object of the present invention is to minimize slippage of a secured intracranial device during use.

Yet another object of the present invention is to enable surgeons to rely on existing fixation skills such as suturing while utilizing the improved fixation device.

A still further object of the present invention is to provide clear visual and/or tactile feedback regarding the quality of fixation.

This invention features a fixation device having a base structure and a fixation structure. In some embodiments, the base structure includes a faceplate having an inferior surface capable of contacting a surface of a skull of a patient, having a superior surface, and defining at least two securement features. Each securement feature is engagable by a cranial fastener to attach the faceplate to the skull. In one embodiment, the fixation structure includes an alignment plate attached to and extending transversely to the inferior surface of the faceplate, positionable within an opening in the skull, and having a superior surface. At least the superior surface of the alignment plate defines at least one channel in which an intracranial device such as an electrode, a catheter or a fiber optic guide is capable of being placed, and further defines at least one fixation feature to enable the intracranial device to be secured to the fixation device.

In some embodiments, the alignment plate has an inferior surface capable of contacting a portion of the wall of a burr hole or other opening in bone, and the alignment plate extends substantially perpendicularly from the faceplate. In certain embodiments, at least one fixation feature is adapted to engage a tension band such as a filament, a tie, an elastic element, or a clip, to secure the intracranial device to the fixation device. In one embodiment, at least one fixation feature includes a hole through which a filament such as a suture is passable to serve as the tension band.

In a number of embodiments, the fixation device further includes at least one tension band, such as a suture or other filament, capable of engaging at least one fixation feature and capable of securing the intracranial device to the fixation device. The fixation device further includes at least two screws serving as cranial fasteners, each screw engaging a securement feature, such as a hole, of the faceplate.

This invention also features a fixation device for which the base structure includes at least one support such as a pin or a strut, and the fixation structure includes a flexible fixation member such as a gasket or ring that is held in position by the support and is tightenable against an intracranial device by a tension member such as a fastener loop.

In some embodiments, the tension member includes a fastener loop that encircles the flexible fixation member and, when tightened, squeezes the fixation member to apply pressure to the intracranial probe. In certain embodiments, a portion of the fastener loop is capable of being tied with a knot that is pushable against the fixation member to maintain fixation of the intracranial probe. In other embodiments, the fixation structure includes a least one ratchet-type mechanism through which a portion of the fastener loop is passable to maintain fixation of the intracranial probe. In another embodiment, the fixation structure includes a mechanism that, when actuated, applies pressure to the fixation member to apply pressure to the intracranial probe.

This invention may also be expressed as an assembly including an intracranial device and a fixation device with a base structure such as a faceplate and a fixation structure such as an alignment plate that are integral in some embodiments and are connected before implantation in other embodiments. The faceplate has an inferior surface capable of contacting a surface of a skull of a patient, having a superior surface, and defines at least two securement features. Preferably, each securement feature is engagable by a cranial fastener to attach the faceplate to the skull, and the alignment plate has a superior surface and an inferior surface, extending transversely to the inferior surface of the faceplate, and positionable within a burr hole or other opening in the skull such that at least a portion of the inferior surface of the alignment plate contacts a portion of the wall of the opening. At least the alignment plate defines at least one channel in which the intracranial device is placed, and further defines a plurality of fixation features by which the intracranial device to secured to the fixation device.

BRIEF DESCRIPTION OF THE DRAWINGS

In what follows, preferred embodiments of the invention are explained in more detail with reference to the drawings, in which:

FIG. 9A is a schematic view of FIG. 9 after tension has been applied to a fixation ring;

DETAILED DESCRIPTION OF THE PRESENTLY PREFERRED EMBODIMENTS

Figure 1:
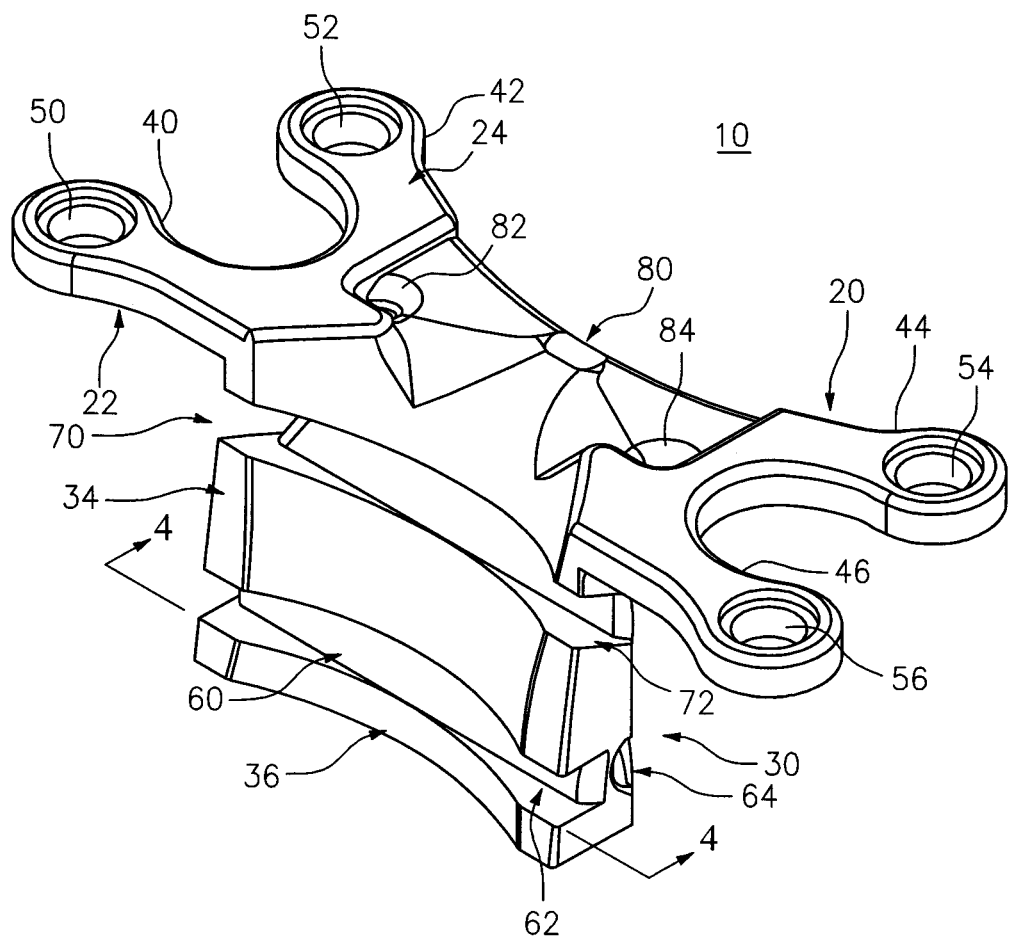
FIG. 1 is a schematic perspective front view of a fixation device according to the present invention.

This invention may be accomplished by a fixation device having a base structure and a fixation structure. In some constructions, the base structure includes a faceplate having an inferior surface capable of contacting a surface of a skull of a patient, having a superior surface, and defining at least two securement features. Each securement feature, such as a hole defined in the faceplate, can be engaged by a cranial fastener such as a screw to attach the faceplate to the skull. In some constructions, the fixation structure of the device includes an alignment plate attached to and extending transversely to the inferior surface of the faceplate, positionable within a burr hole or other opening in the skull, and having a superior surface. At least the superior surface of the alignment plate defines at least one channel in which an intracranial device is capable of being placed, and further defines at least one fixation feature to enable the intracranial device to be secured by at least one tension band, such as a suture, to the fixation device.

In other constructions, as described in more detail below for FIGS. 7-12, the base structure includes at least one support such as a pin or a strut, and the fixation structure includes a flexible fixation member such as a gasket or ring that is held in position by the support and is tightenable against an intracranial device by a tension member such as a fastener loop.

By relying on simple suturing techniques with which surgeons have high degrees of skills and confidence, fixation devices according to the present invention can guide, align and secure intracranial devices with one or more tension bands to achieve simple, rapid and reliable fixation. Other suitable device fasteners serving as tension bands include ties, elastics with a calibrated tension or selected resiliency, and/or clips, including those ties or clips formed to have a memory for a selected shape or tension, to prevent a selected intracranial device secured therewith from moving or shifting its position relative to the fixation device. Examples of different known types of sliding and locking knots and anchoring systems to secure sutures and other filament assemblies are described in U.S. Patent Publication Nos. 2012/0130424 by Sengun et al. and 2013/0261664 by Spenciner et al., for example.

The terms "hole", "burr hole" and "opening" refer herein to any opening in bone made by a burr, a drill bit, a grinder, a trephine, or similar device for removing bone material to create the opening in the bone so that a medical device can be passed through the opening. Formation of circular holes in a cranium is known as trepanning, especially when a trephine instrument is utilized. In particular, burr holes are ground, drilled or scraped in a cranium to reveal the underlying dura mater surrounding the brain. Standard burrs for orthopaedic use including neurosurgery have diameters typically ranging from 0.5 mm to 20 mm and typically rotate at 75,000 to 85,000 RPM (Revolutions Per Minute). Typical diameters for burr holes therefore range from 0.5 mm to at least 20 mm, more typically about 14 mm in diameter, and up to as large an opening as desired when the circumference of the hole is engaged by the burr or trephine to remove a "plug" of cranial bone or to successively widen the burr hole to a selected final diameter for the opening in bone. In addition, burr holes can be expanded using craniotome devices that are inserted into the burr hole and then cut bone parallel to the skull surface.

Figure 2:
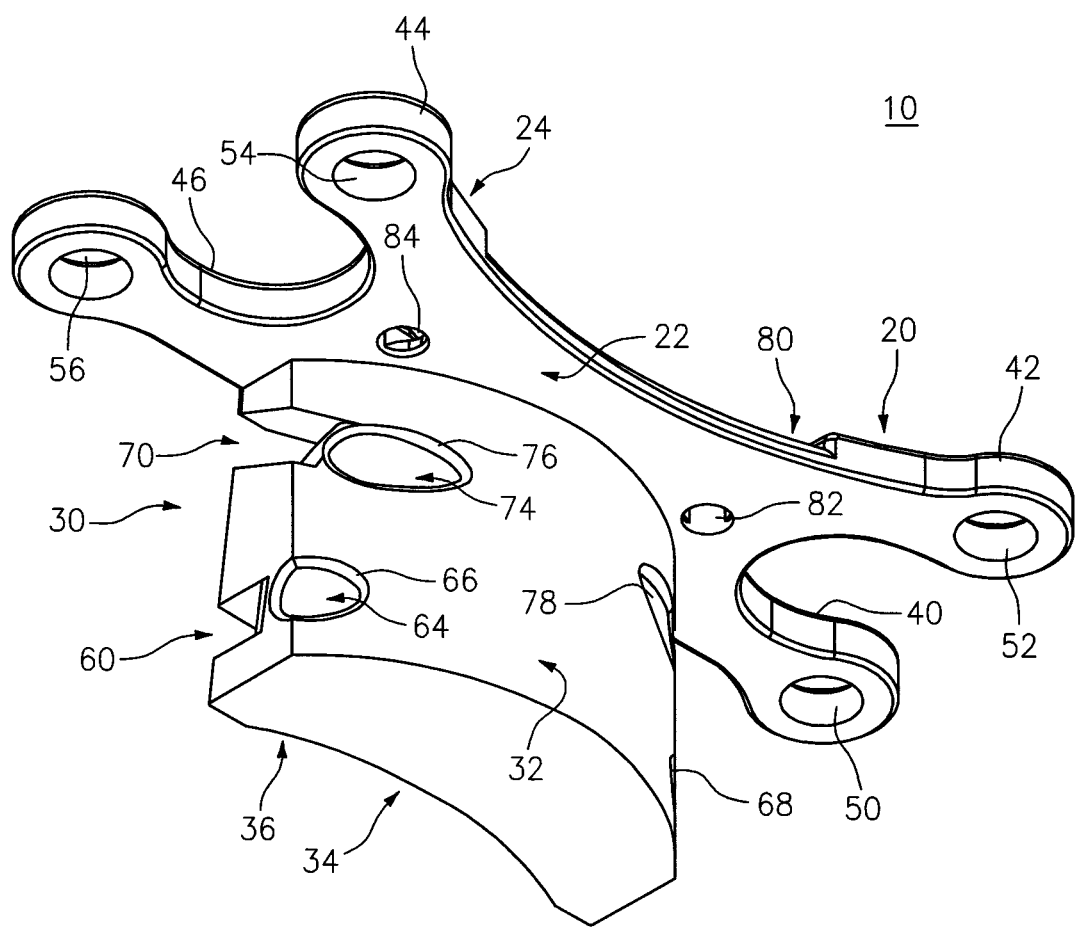
FIG. 2 is a schematic perspective rear view of the device of FIG. 1.
Figure 3:
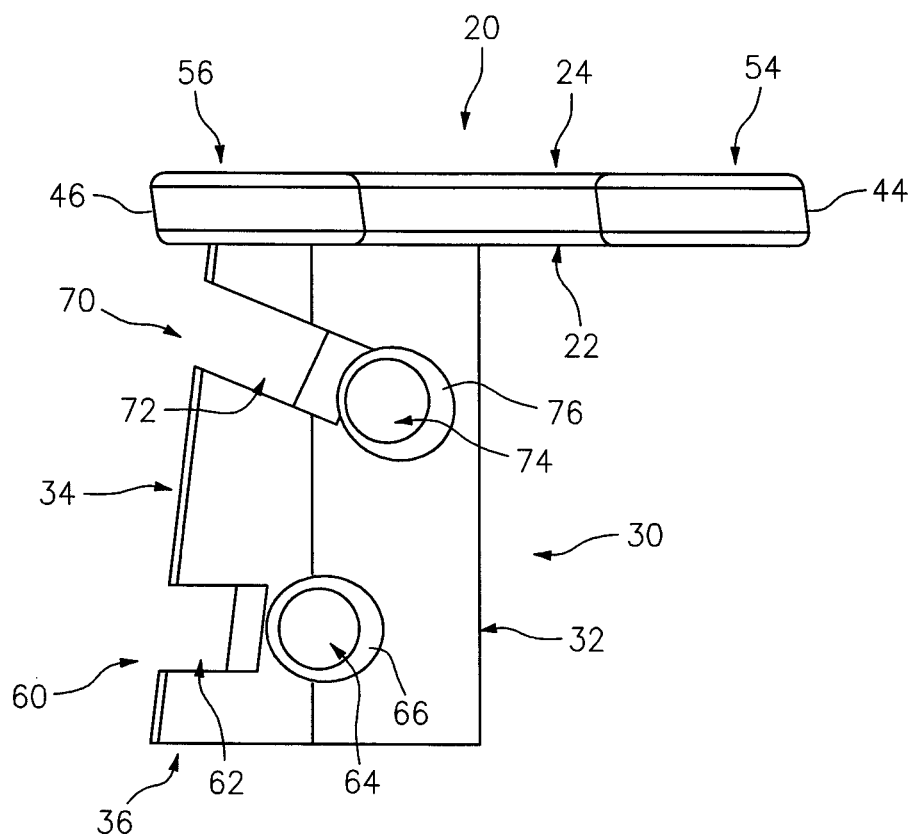
FIG. 3 is a schematic side view of the fixation device of FIG. 1.

Fixation device 10, FIGS. 1-3, is a monolithic low-profile fixation device including a faceplate 20 and an alignment plate 30. Faceplate 20 has an inferior surface 22 capable of contacting a surface of a skull SK of a patient, as described in more detail below in relation to FIG. 5 for assembly 100 including an intracranial device 110. Faceplate 20, FIGS. 1-3, also has a superior surface 24 opposite to the inferior surface 22, and has four arm-like securement features 40, 42, 44 and 46 defining holes 50, 52, 54 and 56, respectively, in this construction. The alignment plate 30 is attached to and extends transversely to the inferior surface 22 of the faceplate 20, preferably substantially perpendicularly or vertically as illustrated best in FIG. 3, and has an inferior surface 32 and a superior surface 34. The alignment plate 30 is positionable within a burr hole BH in skull SK as illustrated best in FIGS. 4 and 5.

At least the superior surface 34 of the alignment plate 30 defines at least one channel 36 in which an intracranial device is capable of being placed, and further defines at least one fixation feature, such as features 60 and 70, to enable an intracranial device to be secured to the fixation device 10. In this construction, fixation features 60, 70 include grooves 62, 72 in superior surface 34 and passages 64, 74 in alignment plate 30 terminating in holes 66, 68 and 76, 78, respectively. The holes 66, 68 and 76, 78 are shown in FIGS. 2 and 3 with beveled or chamfered edges to minimize chafing by one or more tension bands. In other constructions, passages 64, 74 are grooves or recesses formed in the inferior surface 32 instead of tunnel-like passages as illustrated.

Figure 4:
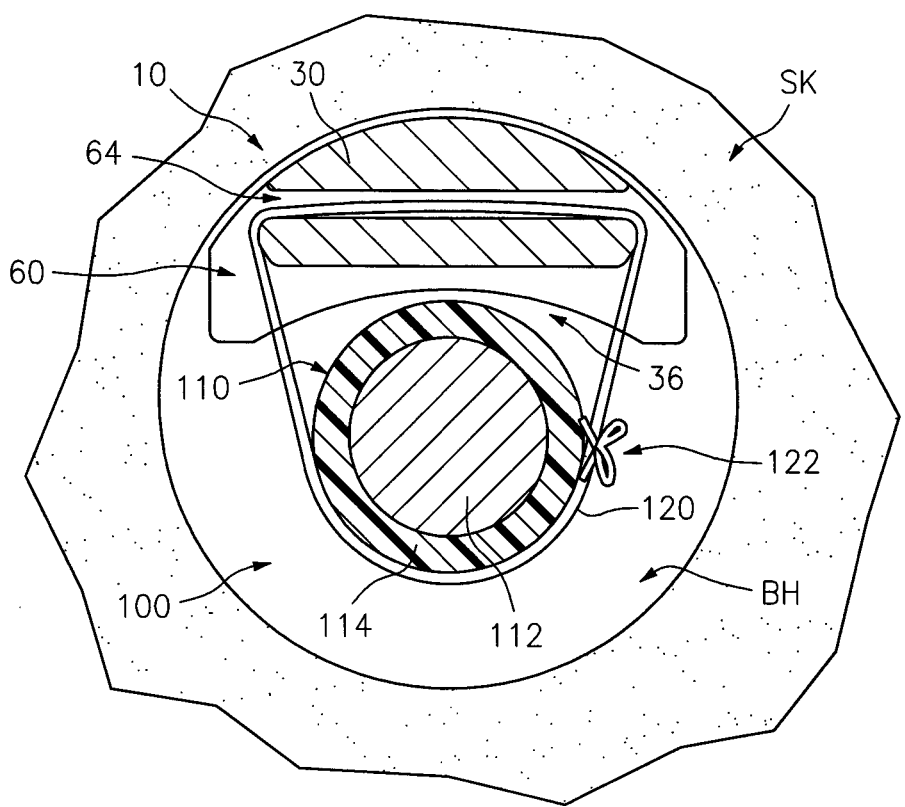
FIG. 4 is a schematic top cross-sectional view along arrows 4 of FIGS. 1-3 of the fixation device positioned within a burr hole in a skull of a patient with an intracranial probe secured by a filament to the fixation device.

Preferably, the inferior surface 32 of the alignment plate 30 is an arc that is matched to the curvature of a selected burr hole. It is preferred that alignment plate 30, when viewed in cross-section along channel 36 such as shown in FIG. 4, occupies less than ¾ of the total cross-sectional area of the burr hole, more preferably less than ⅔ of the total area, and most preferably less than ½ of the total cross-sectional area of the burr hole.

In this construction, faceplate 20 further defines a recess 80 and fixation holes 82 and 84. Preferably, recess 80 is a saddle-like feature that communicates with channel 36 in a continuous manner to enable a proximally-extending portion of an intracranial device to transition from a "vertical" orientation extending into the brain to a "horizontal" orientation lying closely against the faceplate 20 of fixation device 10 and then along the skull of the patient to achieve a low profile in a known orientation and position. In other constructions, posts or other filament engagement features are utilized instead of holes in the faceplate 20. Fixation holes 82 and 84 or similar features assist in maintaining the proximally-extending portion of the intracranial device against the skull and scalp over an extended period of time and during patient activity.

Although a structurally monolithic fixation device is currently preferred for some techniques and procedures, suitable functionally-monolithic devices can be achieved by manufacturing the faceplate separately from the alignment plate and then joining the two components rigidly and fixedly together. Suitable materials for the fixation device, as a monolith or as separate components that are then joined, include metals and metal alloys such as titanium and surgical-grade stainless steel, and polymers such as PEEK (polyether ether ketone). Depending on the material selected, fixation devices can be molded, cast, extruded, thermoformed, or made by additive manufacturing into final device configurations.

Alternatively, the fixation devices start from block or rod forms which have been molded or extruded into initial work piece forms or pre-forms, and are then processed into desired configurations by machining or other known processing technique.

A final assembly 100 of a fixation device 10, an intracranial probe 110 and a tension band 120 is represented in FIG. 4. Assembly 100 is also referred to as a combination, and may be provided to a surgeon as a kit for implantation in a patient. Probe 110 is shown (with an exaggerated diameter for an electrical probe) nestled within channel 36; this concave feature assists holding probe 110 more securely in the center of alignment plate 30 and can assist obtaining and maintaining proper alignment of a distal portion of the probe 110 within the brain of the patient. Visual and/or tactile feedback is provided to health care professionals who can see and/or feel that the intracranial device is securely held in the desired position, including selected depth and orientation for the distal end of the intracranial device.

In this construction, probe 110 includes an electrode 112 and an insulating jacket 114 which represents a coating or a delivery catheter, as is known in the art for such intracranial devices. Other types of intracranial devices that can form an assembly, combination or kit according to the present invention include the various probes, catheters and other neurosurgical devices described in the Background Of The Invention section above.

In this construction, tension band 120 is formed of a suture tied in a knot 122 after passing through passage 64 of fixation feature 60. The intracranial device is secured with at least one tension band after the fixation device 10 is fixedly attached to skull SK in some techniques. In other techniques, the intracranial device 110 is first secured to the fixation device 10, and then the combination 110 is implanted in the patient.

Figure 5:
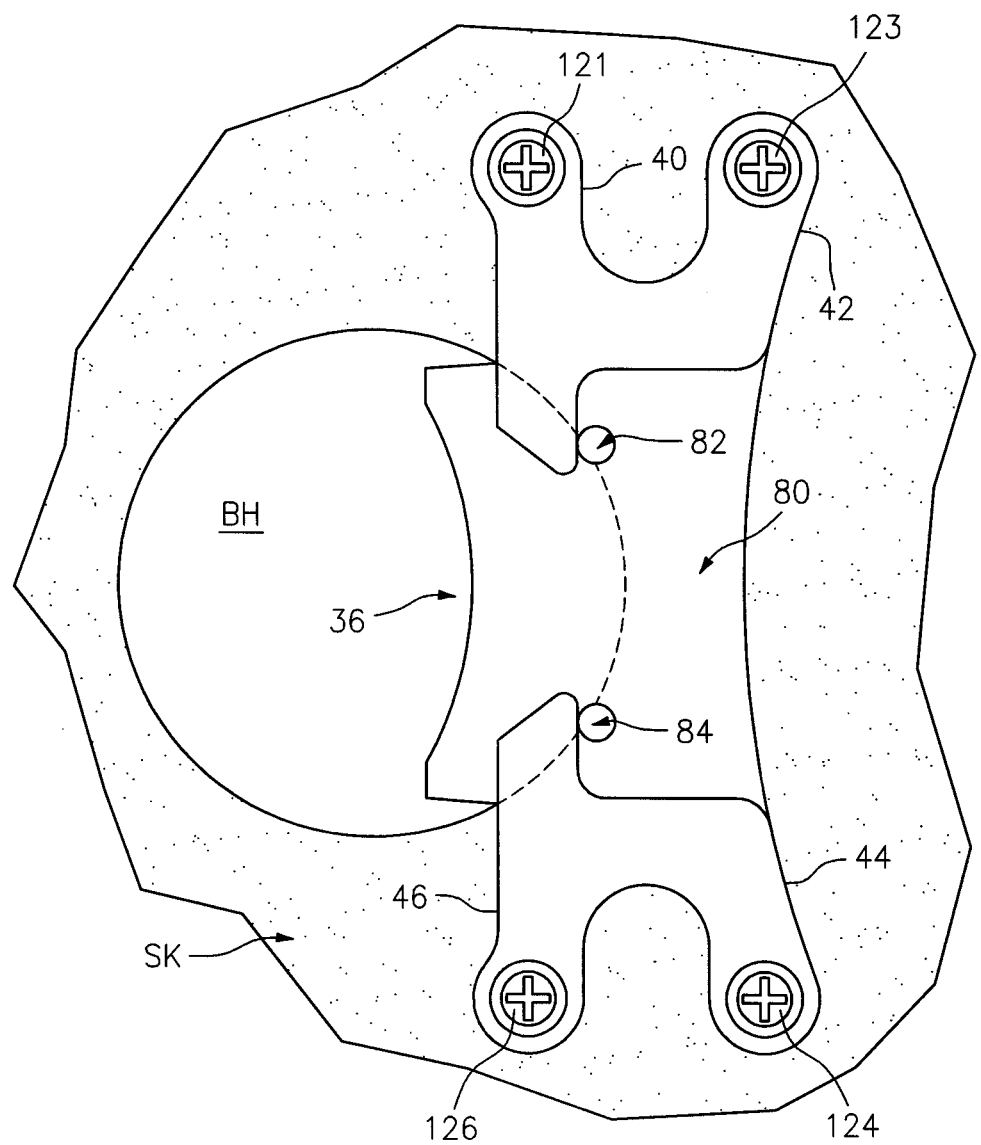
FIG. 5 is a schematic top view of the fixation device of FIG. 4 secured by screws to the skull prior to placement of an intracranial device.

The fixation device itself preferably is secured utilizing a plurality of cranial fasteners such as conventional medical-grade screws. As illustrated in FIG. 5, each securement feature 40, 42, 44 and 46 is engaged by a cranial fastener 121, 123, 124, and 126, respectively, to attach the faceplate 20 to the skull SK. In other constructions, the securement features are notches or other elements that are engagable by screws or other cranial fasteners.

Figure 6:
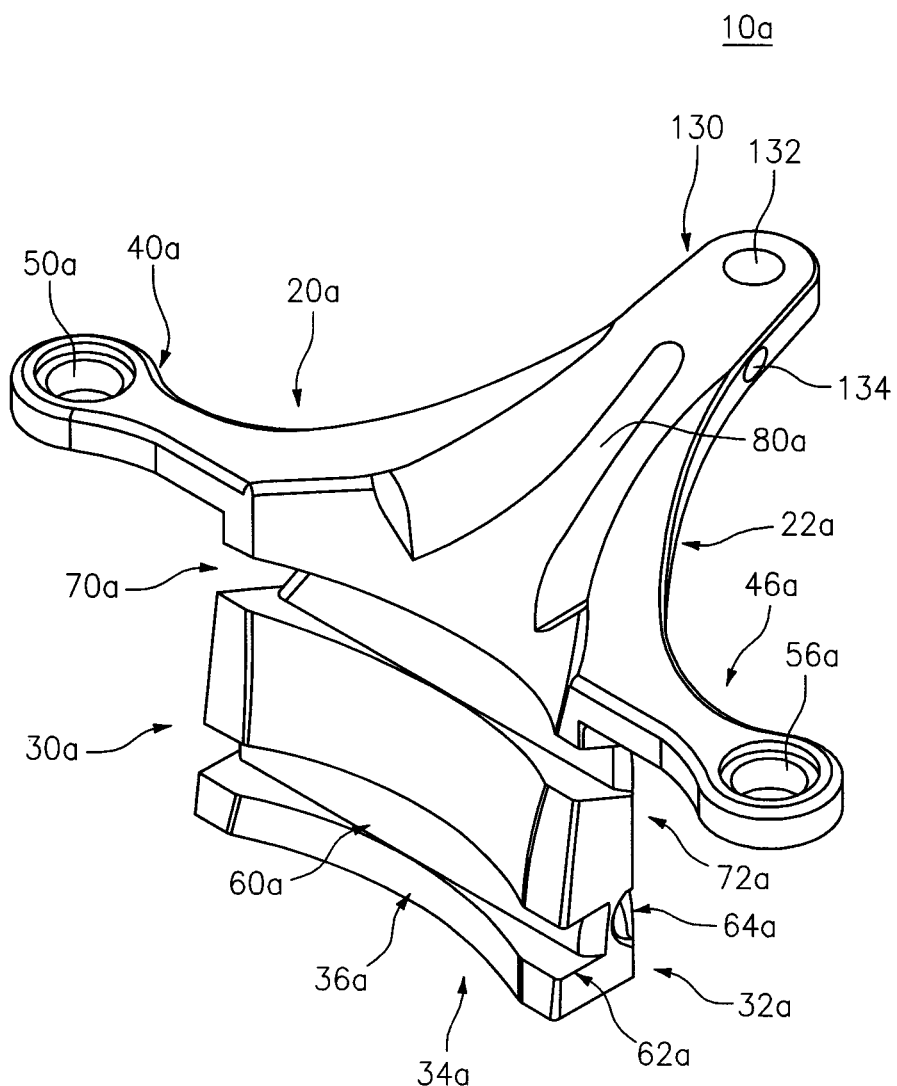
FIG. 6 is a schematic perspective front view of an alternative fixation device according to the present invention.
Figure 7:
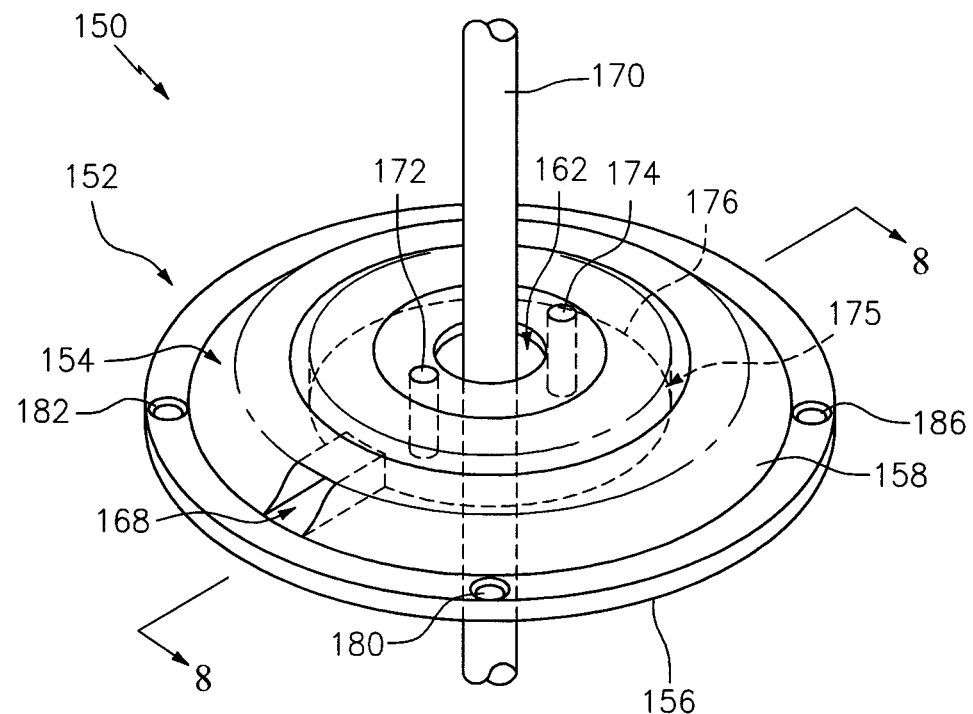
FIG. 7 is a schematic perspective, transparent-type view of another fixation device according to the present invention having a housing with upper and lower openings through which an intracranial device is passed into a burr hole.
Figure 8:
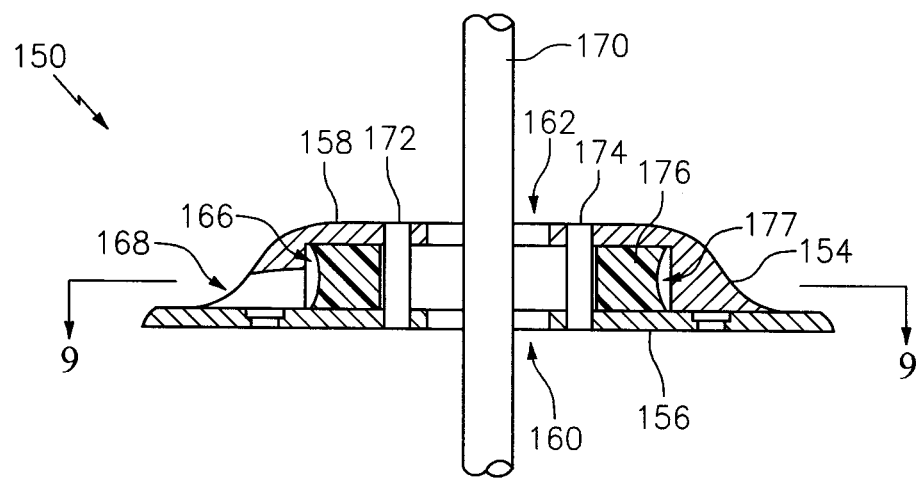
FIG. 8 is a side partial cross-sectional view long lines 8-8 of FIG. 7.
Figure 9:
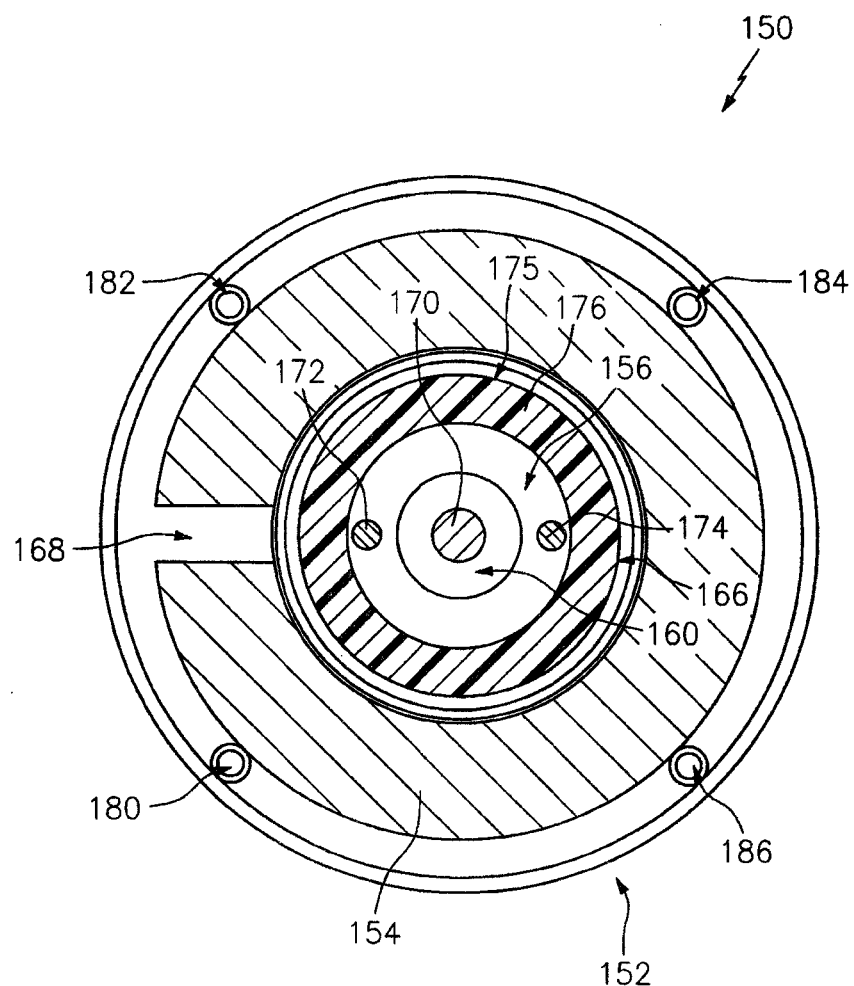
FIG. 9 is a top partial cross-sectional view long lines 9-9 of FIG. 8.
Figure 10:
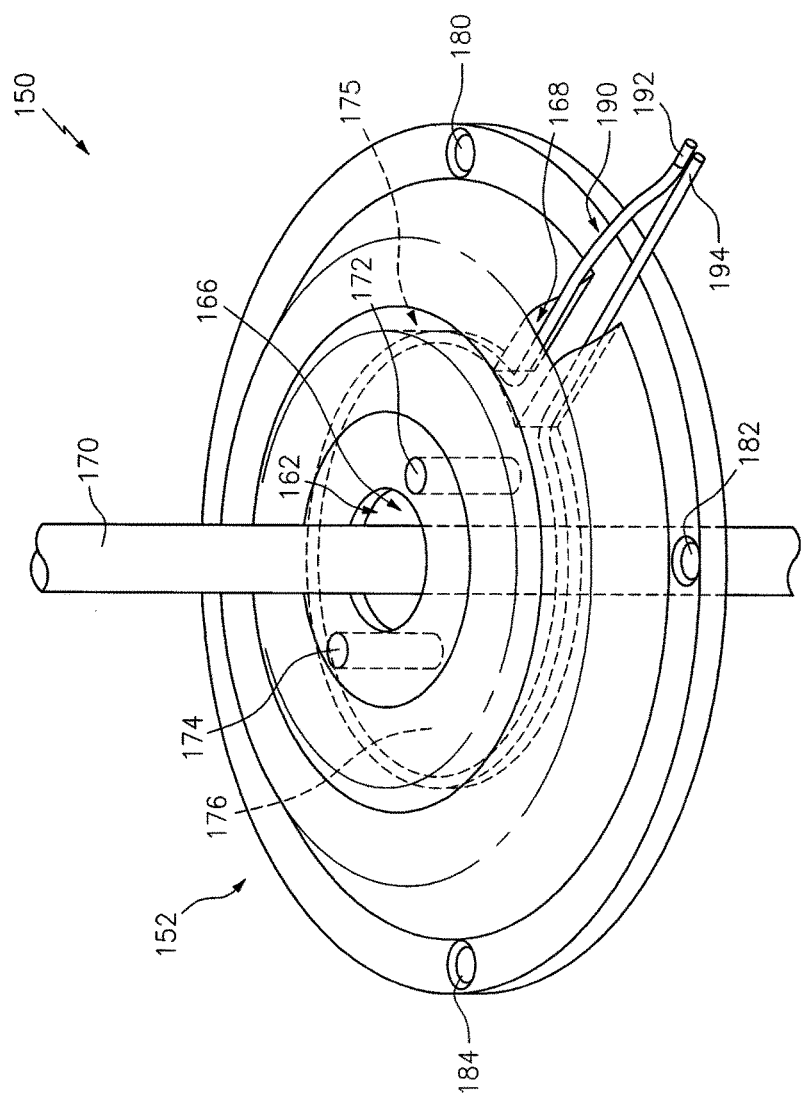
FIG. 10 is a view similar to FIG. 7 showing suture serving as a fastener loop.

While fixation device 10 has been described above having four arms 40, 42, 44 and 46 defining corresponding holes 50, 52, 54 and 56, the number of arms and other features disclosed above are not limitations of the invention. For example, fixation device 10a, FIG. 6, is an alternative monolithic low-profile fixation device including a faceplate 20a and an alignment plate 30a. Faceplate 20a has an inferior surface 22a capable of contacting a surface of a skull of a patient, has a superior surface 24a opposite to the inferior surface 22a, and has three arm-like securement features 40a, 46a and 130 defining holes 50a, 56a and 132, respectively, in this construction.

Recess 36a in alignment plate 30a merges with recess 80a in faceplate 20a. A feature 134 such as a passage, a groove, or other fixation element enables the proximally-extending portion of an intracranial device to be anchored against arm 130 of faceplate 20a to further reduce the profile of the combination of fixation device 10a and an intracranial device secured thereto.

The alignment plate 30a is attached to and extends transversely to the inferior surface 22a of the faceplate 20a, preferably substantially perpendicularly or vertically, and has an inferior surface 32a and a superior surface 34a. The alignment plate 30a is positionable within a burr hole in a skull and further defines at least one fixation feature, such as features 60a and 70a, to enable an intracranial device to be secured to the fixation device 10a. In this construction, fixation features 60a, 70a include grooves 62a, 72a in superior surface 34a and channels 64a, 74a (not shown) in alignment plate 30a, respectively.

In other constructions, such as illustrated in FIGS. 7-10 for fixation device 150 according to the present invention, base structure 152 includes a housing 154 with a base-plate 156 and an upper portion 158 that define lower and upper openings 160 and 162, respectively, through which an intracranial device 170 is passed into a burr hole (not shown). In this construction, base-plate 156 and upper portion 158 hold support pins 172 and 174 that control alignment of a flexible fixation ring 176 as described in more detail below. The fixation ring 176 lies within a cavity 166, FIGS. 8 and 9, which is accessible through a passage 168, as described in more detail below; both cavity 166 and passage 168 are defined in upper portion 158.

Base-plate 156 further defines securement openings 180, 182, 184 and 186 through which cranial fasteners such as medical-grade screws are insertable. In some constructions, base-plate 156 and upper portion 158 are formed as a single monolithic component 154, such as by additive manufacturing; fixation ring 176 and support pins 172, 174 are inserted through respective openings in monolithic housing 154. In other constructions, base-plate 156 and upper portion 158 are formed of separate components, which are easy to mass-produce via injection molding when formed of a medical-grade polymer.

Fixation structure 175 includes the flexible fixation ring 176, which is formed in some constructions of a resilient and/or deformable material such as an elastomeric rubber-type material. Fixation ring 176 preferably defines a recess, channel or concavity 177 as shown in cross-section in FIG. 8 and as shown perspective view in FIG. 10 engaging a tension member 190. In this construction, tension member 190 is a filament such as a suture that is wrapped around fixation ring 176 within cavity 166 and has segments or legs 192 and 194 extending through passage 168

In some constructions, such as described above in relation to FIG. 10, the tension member includes a fastener loop that encircles the flexible fixation member and, when tightened, squeezes the fixation member to apply pressure to the intracranial probe. In certain constructions, a portion of the fastener loop is capable of being tied with a knot that is pushable against the fixation member to maintain fixation of the intracranial probe. In other constructions, fixation structure 175 includes a least one post, preferably including a ratchet-type mechanism through which a portion of the fastener loop is passable, to maintain fixation of the intracranial probe. In another constructions, the fixation structure includes a mechanism that, when actuated, applies pressure to the fixation member to apply pressure to the intracranial probe.

Figure 11:
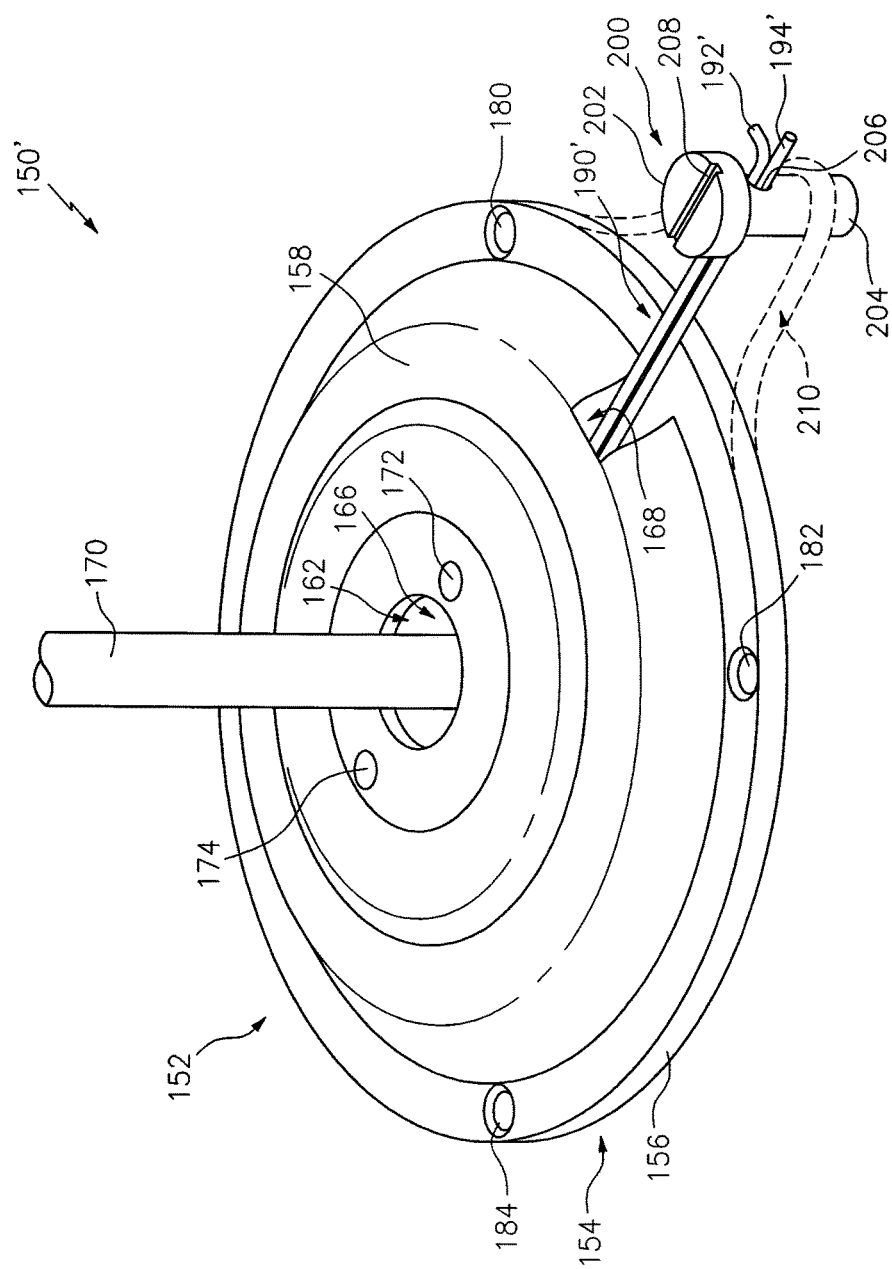
FIG. 11 is a solely exterior perspective view of the fixation device of FIG. 7 with a tension mechanism to tighten and/or secure the legs of a fastener loop.
Figure 12:
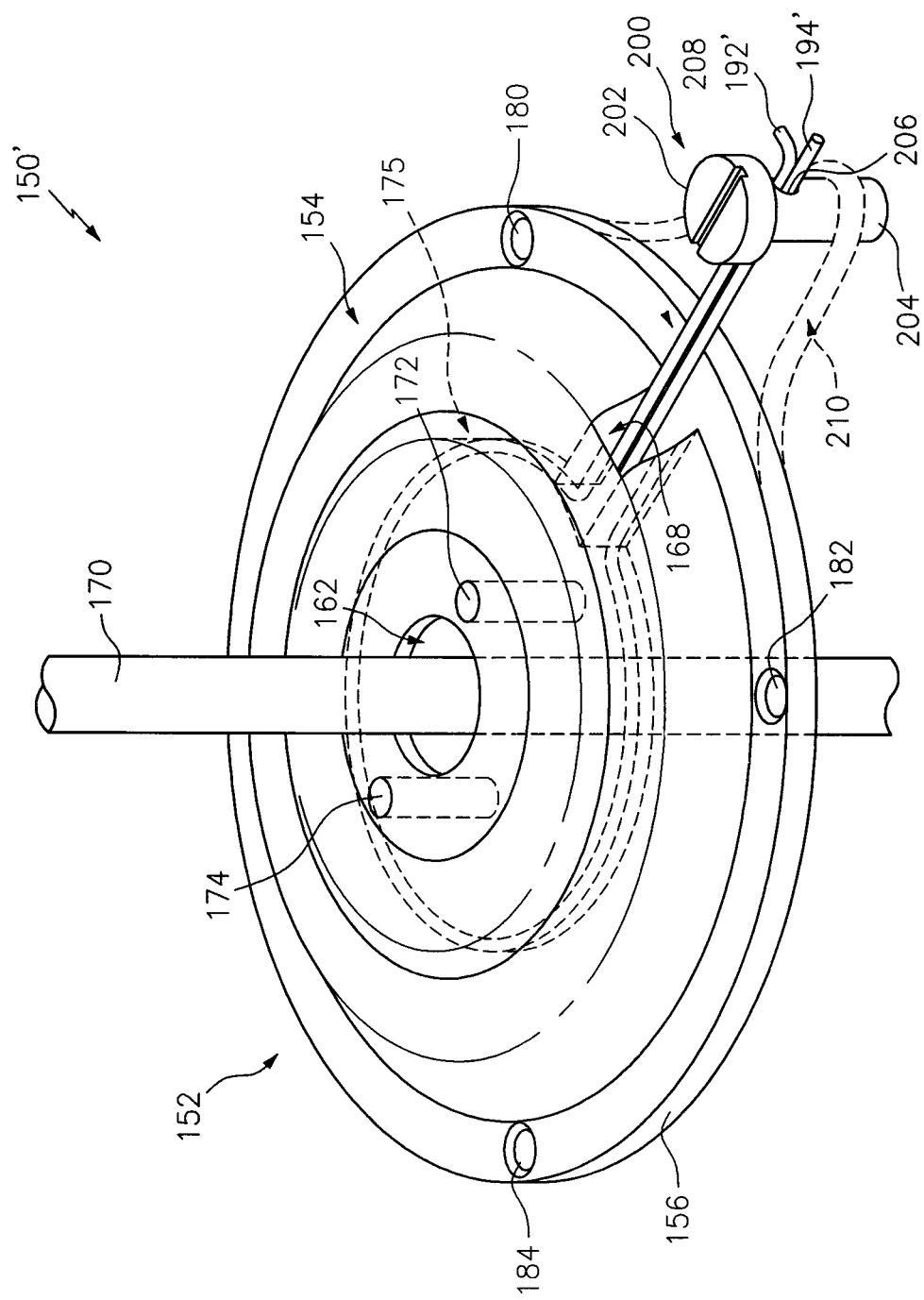
FIG. 12 is a transparent-type view of FIG. 11.

Fixation system 150' according to the present invention, FIGS. 11-12, includes the base structure 152 and fixation structure 175 as described above in relation to FIGS. 7-10, and further includes a post 200 having an enlarged head 202 and a shaft 204 defining a passage 206 through which legs 192' and 194' of filament 190' are passed. In some constructions, post 200 is a separate, independent screw-type component that is inserted into the skull a desired distance from passage 168 defined by upper portion 158. In other constructions, base structure 152 includes extension 210, shown in phantom, which holds post 200 in a fixed, spaced condition from passage 168. In yet other constructions, the post 200 is integrated within upper portion 158 to maintain the low profile of housing 154. In this construction, post head 202 defines a slot 208 into which a tool is insertable to increase or decrease tension on filament legs 192' and 194'. In constructions where post 200 includes a ratchet-type mechanism, a release lever enables a user to disengage a pawl from a sawtooth gear or a high-friction surface which serves as an anti-backlash mechanism.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A fixation device comprising:
a base structure having a housing with a base plate capable of contacting a surface of a skull of a patient, having an upper portion, and defining at least two securement features, each securement feature engagable by a cranial fastener to attach the base structure to the skull;
a fixation structure carried by the base structure and positionable at least one of (i) over an opening in the skull and (ii) within an opening in the skull; and
wherein at least one surface of the fixation structure defines at least one channel in which an intracranial device is capable of being placed, and the fixation structure further includes at least one fixation feature to enable the intracranial device to be secured to the fixation device; and
wherein the base structure includes at least one support, and the fixation structure includes a flexible fixation member that: (1) is formed of a material that is at least one of resilient and deformable; (2) is held in position by the support at least over the opening in the skull; and (3) is tightenable against the intracranial device by a tension member to apply pressure to the intracranial device after the intracranial device is passed through the flexible fixation member, wherein the fixation structure further includes a post held at a fixed, spaced condition from the flexible fixation member, and the tension member includes a fastener loop that encircles the flexible fixation member and, when the tension member is tightened and secured to the post, the fastener loop squeezes the fixation member to apply pressure to the intracranial device.

2. A fixation device comprising:
a base structure having a housing with a base plate capable of contacting a surface of a skull of a patient, having an upper portion, and defining at least one support and at least two securement features, each securement feature engagable by a cranial fastener to attach the base structure to the skull; and
a fixation structure carried by the base structure and positionable at least over an opening in the skull, the fixation structure including a flexible elastomeric fixation member that is held in position by the support at least over the opening in the skull and is tightenable by a tension member against an intracranial device passed through the flexible fixation member and placed into the opening in the skull to hold the intracranial device in a fixed position by applying pressure to the intracranial device, wherein the fixation structure further includes a post held at a fixed, spaced condition from the flexible fixation member, and the tension member includes a fastener loop that encircles the flexible fixation member and, when the tension member is tightened and secured to the post, the fastener loop squeezes the fixation member to apply pressure to the intracranial device.

3. The fixation device of claim 2 wherein the housing surrounds the flexible fixation member.

4. The fixation device of claim 2 wherein the tension member is a filament and a portion of the fastener loop is capable of being tied with a knot that is pushable against the fixation member to maintain fixation of the intracranial device.

5. The fixation device of claim 2 further including a least one ratchet-type mechanism through which a portion of the fastener loop is passable to maintain fixation of the intracranial device.

6. The fixation device of claim 2 further including a mechanism that, when actuated, applies pressure to the fastener loop to apply pressure to the fixation member to apply pressure to the intracranial device.

\* \* \* \* \*